(12) United States Patent
Shimko et al.

(10) Patent No.: US 9,034,052 B2
(45) Date of Patent: May 19, 2015

(54) DELIVERY SYSTEMS CONTAINING BIOACTIVE MATERIALS

(71) Applicant: Warsaw Orthopedic, Inc., Warsaw, IN (US)

(72) Inventors: Daniel A. Shimko, Germantown, TN (US); Kerem N. Kalpakci, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/740,357

(22) Filed: Jan. 14, 2013

(65) Prior Publication Data

US 2014/0200676 A1    Jul. 17, 2014

(51) Int. Cl.
*A61F 2/28* (2006.01)
*A61F 2/46* (2006.01)
*A61F 2/30* (2006.01)

(52) U.S. Cl.
CPC ..... *A61F 2/2846* (2013.01); *A61F 2002/30588* (2013.01); *A61F 2002/30738* (2013.01); *A61F 2/4601* (2013.01)

(58) Field of Classification Search
CPC ............ A61F 2002/30588; A61F 2002/30738
USPC .......................................... 623/23.52–23.54
See application file for complete search history.

(56) References Cited

U.S. PATENT DOCUMENTS

| | | | |
|---|---|---|---|
| 5,501,706 A * | 3/1996 | Arenberg | 623/23.56 |
| 5,549,679 A * | 8/1996 | Kuslich | 623/17.12 |
| 6,294,187 B1 | 9/2001 | Boyce et al. | |
| 6,440,444 B2 | 8/2002 | Boyce et al. | |
| 6,478,825 B1 | 11/2002 | Winterbottom et al. | |
| 6,696,073 B2 | 2/2004 | Boyce et al. | |
| 7,083,648 B2 | 8/2006 | Yu et al. | |
| 7,618,457 B2 * | 11/2009 | Hudgins | 623/17.12 |
| 7,749,267 B2 * | 7/2010 | Karmon | 623/16.11 |
| 7,985,414 B2 | 7/2011 | Knaack et al. | |
| 8,042,688 B2 | 10/2011 | Parks et al. | |
| 8,277,828 B2 * | 10/2012 | Fischer | 424/422 |
| 2003/0153976 A1 * | 8/2003 | Cauthen et al. | 623/17.16 |
| 2005/0251267 A1 | 11/2005 | Winterbottom et al. | |
| 2005/0283255 A1 | 12/2005 | Geremakis et al. | |
| 2006/0052879 A1 | 3/2006 | Kolb | |

(Continued)

OTHER PUBLICATIONS

U.S. Appl. No. 13/358,585, filed Jan. 26, 2012.

*Primary Examiner* — David H Willse
*Assistant Examiner* — Javier Blanco
(74) *Attorney, Agent, or Firm* — Sorell Lenna & Schmidt LLP (57) ABSTRACT

A delivery system comprising a covering containing at least a first substance for release to a surgical site is provided. The covering includes an elongated containment portion having at least one compartment, wherein the covering includes an elongated containment having a first end and a second end. At one end the elongated containment defines an opening configured to receive at least one substance. The at least one substance can be DBM or a mixture of demineralized fibers and particles in a ratio of 30:70. The delivery system also includes a closing member that can close the elongated containment prior to insertion at a surgical site. The closing member can be drawing strings, stitches, sutures, wing sutures, heat seals, adhesion, pressure fittings, coil ring, twist tie. The substance contained in the delivery system can also be enclosed by twisting and folding over a portion of the covering.

10 Claims, 3 Drawing Sheets

(56) References Cited

U.S. PATENT DOCUMENTS

| | | |
|---|---|---|
| 2006/0216323 A1 | 9/2006 | Knaack et al. |
| 2007/0088443 A1 | 4/2007 | Hanssen et al. |
| 2007/0098756 A1 | 5/2007 | Behnam |
| 2007/0110820 A1 | 5/2007 | Behnam |
| 2007/0191963 A1 | 8/2007 | Winterbottom et al. |
| 2008/0091270 A1 | 4/2008 | Miller et al. |
| 2008/0262630 A1* | 10/2008 | Fulmer et al. ............... 623/23.52 |
| 2009/0130173 A1 | 5/2009 | Behnam et al. |
| 2009/0157087 A1* | 6/2009 | Wei et al. ........................ 606/99 |
| 2011/0054408 A1 | 3/2011 | Wei et al. |
| 2011/0108644 A1 | 5/2011 | Morris et al. |

* cited by examiner

DELIVERY SYSTEMS CONTAINING BIOACTIVE MATERIALS

FIELD

A delivery system for delivering a substance or material to a surgical site is provided. More particularly, a delivery system comprising a covering, a substance, and a closing member.

BACKGROUND

The use of bone grafts and bone substitute materials in orthopedic medicine is known. While bone wounds can regenerate without the formation of scar tissue, fractures and other orthopedic injuries take a long time to heal, during which time the bone is unable to support physiologic loading unaided. Metal pins, screws, rods, plates and meshes are frequently required to replace the mechanical functions of injured bone. However, metal is significantly more stiff than bone. Use of metal implants may result in decreased bone density around the implant site due to stress shielding. Physiologic stresses and corrosion may cause metal implants to fracture. Unlike bone, which can heal small damage cracks through remodeling to prevent more extensive damage and failure, damaged metal implants can only be replaced or removed. The natural cellular healing and remodeling mechanisms of the body coordinate removal of bone and bone grafts by osteoclast cells and formation of bone by osteoblast cells.

Conventionally, bone tissue regeneration is achieved by filling a bone repair site with a bone graft. Over time, the bone graft is incorporated by the host and new bone remodels the bone graft. In order to place the bone graft, it is common to use a monolithic bone graft or to form an osteoimplant comprising particulated bone in a carrier. The carrier is thus chosen to be biocompatible, to be resorbable, and to have release characteristics such that the bone graft is accessible.

The rapid and effective repair of bone defects caused by injury, disease, wounds, or surgery is a goal of orthopedic surgery. Toward this end, a number of compositions and materials have been used or proposed for use in the repair of bone defects. The biological, physical, and mechanical properties of the compositions and materials are among the major factors influencing their suitability and performance in various orthopedic applications.

Demineralized bone matrix ("DBM") implants have been reported to be particularly useful. Demineralized bone matrix is typically derived from cadavers. The bone is removed aseptically and/or treated to kill any infectious agents. The bone is then particulated by milling or grinding and then the mineral components are extracted for example, by soaking the bone in an acidic solution.

Current DBM formulations have various drawbacks. First, while the collagen-based matrix of DBM is relatively stable, the active factors within the DBM matrix are rapidly degraded. The osteogenic activity of the DBM may be significantly degraded within 24 hours after implantation, and in some instances the osteogenic activity may be inactivated within 6 hours. Therefore, the factors associated with the DBM are only available to recruit cells to the site of injury for a short time after transplantation. For much of the healing process, which may take weeks to months, the implanted material may provide little or no assistance in recruiting cells.

Attempts to overcome these problems have lead researchers to utilize delivery systems such as polymer mesh bags or pouches to release DBM at a surgical site. Pouch closure is typically done by suturing, which is often time consuming and may require special equipment to bring about pouch closure.

Thus, there is a need to improve the efficacy and consistency of DBM delivery systems by utilizing more expeditious and simpler approaches to closing the open end of a DBM containing polymer mesh bag.

SUMMARY

A delivery system for delivering a substance or material to a surgical site is provided. The delivery system comprises a covering and a substance to be retained within and delivered by the covering. Generally, the covering may be at least a single compartment capable of retaining a substance provided therein until the covering is placed at a surgical site. In some examples, upon placement, the covering facilitates transfer of the substance and/or materials from the covering to the surgical site. The covering may participate in, control, or otherwise adjust, the release of the substance or penetration of the covering by surrounding materials, such as cells or tissues.

In certain embodiments the covering of the delivery system includes an elongated containment portion having at least one compartment and at least a first substance which can be mixed with another substance prior to delivery at a surgical site. The first substance can be particles, fibers or chips of demineralized bone matrix (DBM) and the second substance can be bone graft material such as autologous milled bone particles and growth factors.

In some embodiments, the delivery system comprises a closing member that can be attached at any location along the elongated container. In various embodiments, the closing member can be attached at a location effective to define an upper and lower portion of the elongated containment. In other embodiments, after securing the elongated containment with the closing member, the upper portion can be folded over the lower portion of the elongated containment. In yet other embodiments, the upper portion of the elongated containment can be folded over the lower portion in the absence of a closing member, simply by twisting the upper portion at a selected location and folding over the lower portion of the elongated containment.

In various embodiments, the closing member comprises drawing strings, stitches, sutures, wing sutures, heat seals, adhesion, pressure fittings, coil ring, twist tie or combinations thereof. In certain embodiments, either the covering or the closing member or both comprise a material selected from bioerodible polymers, bioabsorbable polymers, biodegradable biopolymers, synthetic polymers, copolymers or combinations thereof.

In some embodiments, the elongated containment portion has a cross sectional shape selected from generally circular or generally oval and a shape that can be tubular, rectangular, or cubic. The covering can have two ends opposite each other and be made from porous mesh to provide, for example, a porous mesh bag.

In various embodiments, the at least one compartment is unfilled at manufacture but configured to be filled prior to or during the surgical procedure.

In other embodiments, the at least one compartment of the delivery system can be filled with autograft or allograft. In certain embodiments, the at least one substance in the at least one compartment comprises demineralized bone matrix fibers and particles in a ratio of about 30:70.

In various embodiments, a second substance can be added to the delivery systems described herein includes protein, bone morphogenetic proteins, carbohydrate, lipids, collagen, allograft bone, autograft bone, tricalcium phosphate, hydroxyapatite, growth and differentiation factors, carriers for growth factors, growth factors extracts of tissue, bone marrow aspirate, concentrates of lipid derived or marrow derived adult stem cells, umbilical cord derived stem cells, committed or partially committed cells from osteogenic or chondrogenic lineage, antimicrobials, antibiotics, or combinations thereof.

In certain embodiments, a delivery system comprising a covering configured for implantation into a bone defect site is provided. The covering contains at least one compartment having an elongated containment with a first end and second end opposite each other, the elongated containment defining an opening configured to receive at least one substance. In many embodiments, the elongated containment is adapted to receive slidably a closing member at a selected location along the elongated containment, the selected location effective to define around the closing member an upper and a lower portion of the containment, the upper portion foldable over the lower portion.

In various embodiments, the present application provides a method for preparing a delivery system comprising a covering for implantation into a bone defect. The method for preparing the delivery system comprises providing the covering having an elongated containment and defining an opening at one end, the opening configured for receiving at least one substance. Subsequently, the method includes filling the elongated containment with the at least one substance, closing the elongated containment with a closing member at a selected location along the elongated containment, and implanting the closed delivery system into a bone defect.

The present application also provides a method for treating a bone defect in a patient in need of such treatment. The method of treatment comprises implanting into the bone defect all or at least a portion of a covering comprising one or more biodegradable polymers, the covering being porous and comprising at least one compartment, the at least one compartment comprising an elongated containment, which elongated containment defines an opening configured to receive at least one substance, the elongated containment adapted to receive slidably a closing member at a selected location along the elongated containment.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

BRIEF DESCRIPTION OF THE DRAWINGS

In part, other aspects, features, benefits and advantages of the embodiments will be apparent with regard to the following description, appended claims and accompanying drawings where:

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

The headings below are not meant to limit the disclosure in any way; embodiments under any one heading may be used in conjunction with embodiments under any other heading.

DEFINITIONS

It is noted that, as used in this specification and the appended claims, the singular forms "a," "an," and "the," include plural referents unless expressly and unequivocally limited to one referent. For example, reference to "a compartment" includes one, two, three or more compartments.

Bioactive Agent or Bioactive Compound, as used herein, refers to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anticholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, antisecretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996; and the United States Pharmacopeia-25/National Formulary-20, published by the United States Pharmcopeia Convention, Inc., Rockville Md., 2001, each of which is incorporated herein by reference.

Biocompatible, as used herein, refers to materials that, upon administration in vivo, do not induce undesirable long-term effects.

Bone, as used herein, refers to bone that is cortical, cancellous or cortico-cancellous of autogenous, allogenic, xenogenic, or transgenic origin.

Demineralized, as used herein, refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the invention. In some embodiments, demineralized bone has less than 95% of its original mineral content. Demineralized is intended to encompass such expressions as "substantially demineralized," "partially demineralized," and "fully demineralized."

Demineralized bone matrix, as used herein, refers to any material generated by removing mineral material from bone tissue. In preferred embodiments, the DBM compositions as used herein include preparations containing less than 5% calcium and preferably less than 1% calcium by weight. Partially demineralized bone (e.g., preparations with greater than 5% calcium by weight but containing less than 100% of the original starting amount of calcium) are also considered within the scope of the invention.

Osteoconductive, as used herein, refers to the ability of a non-osteoinductive substance to serve as a suitable template or substance along which bone may grow.

Osteogenic, as used herein, refers to the ability of an agent, material, or implant to enhance or accelerate the growth of new bone tissue by one or more mechanisms such as osteogenesis, osteoconduction, and/or osteoinduction.

Osteoimplant, as used herein, refers to any bone-derived implant prepared in accordance with the embodiments of this invention and therefore is intended to include expressions such as bone membrane, bone graft, etc.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

Superficially demineralized, as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

I. Introduction

A delivery system for delivering a substance or material to a surgical site is provided. In various embodiments, the delivery system comprises a covering and a substance for delivery by the covering. The covering provides a superior containment of the substance, such as graft material, which helps focus and concentrate materials that provide healing at the surgical site. In some embodiments, the covering also helps the surgeon perform less invasive procedures, by delivering a contained unit of grafting material to the surgical site.

The delivery system may be used to treat a wide variety of bone or soft tissue defects including surgically created or pre-existing (such as by trauma) defects. In some embodiments, the delivery system may be used to treat contained bony voids or contained defects. Such bony voids are voids or cavities that have a cortical shell on three sides. In some embodiments, the delivery system may be used to treat critical defects. Generally, critical defects are defects that will not heal spontaneously and must be grafted in order to assure healing. In some embodiments, the delivery system may be used to treat segmental defects. Segmental defects are defects in the cortical shaft of a long bone in which a segment is missing. In some embodiments, the delivery system may be used to treat contained or non-critical defects wherein the delivery system may act as a plug to assist healing. Other applications for the delivery system are discussed herein and none are intended to be limiting.

The delivery system comprises a covering and a substance wherein the substance is provided within the covering for delivery to the surgical site. The delivery system provides increased handling properties, ability to place grafting material reliably using minimally invasive procedures, and improved delivery characteristics such as graft retention compared with other systems. In some embodiments, upon placement, the covering facilitates transfer of the substance and/or materials to the surgical site. In some embodiments, for example wherein the covering holds graft materials, the covering substantially prevents graft migration. The covering may participate in, control, or otherwise adjust, the release of the substance from the covering or penetration of the covering by surrounding materials, such as cells or tissues.

Generally, the covering may be a single or multi-compartment structure capable of at least partially retaining a substance provided therein until the covering is placed at a surgical site. In some embodiments, the covering may be substantially non-expandable or minimally deformable. In some embodiments, the covering may be a temporary covering wherein the covering is substantially resorbable. For example, in some embodiments, the covering may be formed of a material that is substantially resorbed within 2 weeks, within 4 weeks, within 12 weeks, or within other suitable time frame. Accordingly, in some embodiments a delivery system including the covering may be a temporary delivery system. The covering may include one or more attachment mechanisms for retaining the covering at the surgical site. The attachment mechanism may be a mechanical attachment mechanism, a physical attachment mechanism, a biological attachment mechanism or a chemical attachment mechanism, or may employ combinations of these. The attachment mechanism may be used to attach the covering to skeletal or soft tissue proximate the surgical site.

In some embodiments, the covering may be used for containment of particulate or morselized materials (the substance provided in the covering), optionally to provide a focus or concentration of biological activity. In some embodiments, the covering may be used for containment of a substance one or more of bone particles, bone fibers, other osteoinductive or osteoconductive materials, BMP, antibiotics, or other materials.

In some embodiments, the covering may be used for maintaining materials (the substance provided in the covering) in spatial proximity to one another, possibly to provide a synergistic effect. In some embodiments, the covering may be used to control availability of a substances provided within the covering to cells and tissues of a surgical site over time. In some embodiments, the covering may be used for delivery through a limited opening, such as in minimally invasive surgery or mini-open access. In some embodiments, the covering may be used to deliver morselized or particulated materials (the substance provided in the covering) in pre-measured amounts. In other embodiments, the substance may be liquid or flowable, or combinations of these with particulate, morselized, and/or other materials.

In various embodiments, the covering may contain a substance or material such as a graft material. The covering limits, and in some embodiments eliminates, graft migration and maintains graft density. The delivery system, with contained substance or material, may be configured to conform to surrounding bony contours or implant space. In some embodiments, the delivery system provides a pathway for healing/cell penetration and tissue ingrowth. Thus, the covering may facilitate transfer or diffusion of materials into and out of the covering. For example, the covering may facilitate diffusion from the covering of a substance provided within the covering or may facilitate diffusion into the covering of materials in the surgical site, such as cells and tissues, into the covering. The covering may be configured to permit diffusion of some materials while substantially preventing diffusion of other materials. Further, in various embodiments, the covering may be configured such that diffusion is permitted into or out of certain portions of the covering but not other portions of the covering. In some embodiments, the covering may merely retain a substance at the surgical site.

II. Covering Material

The covering may comprise a structural material and, in some embodiments, a functional material. The structural material may comprise a mesh material, a polymeric material, a substantially or other. The functional material may comprise, for example, a radiopaque material, a bacteriocidal material, or other.

Structural Material Characteristics

In various embodiments, in accordance with the specific application for which the covering is being used, the covering may be flexible, may be non-elastic, or may be elastic. The covering material may be braided, woven, non-woven shape memory, particulate, threaded, porous, non-porous, or substantially solid. While the term "structural" is used to describe the material forming the main structure of the covering, it is to be appreciated that this is not intended to imply that the covering need have structural or load-bearing characteristics.

The covering may participate in, control, facilitate, prevent, or otherwise adjust the release of the substance. For example, the covering may act as a selectively permeable membrane and/or may be porous, with the level of porosity being related to the nature of the substances inside the covering. Thus, the material for and configuration of the covering may be selected or adjusted based on desired release characteristics. Specific properties of the structural material that may be adjusted include thickness, permeability, porosity, strength, flexibility, elasticity, and others. It is to be appreciated that some of these properties may depend on others. For example, the thickness and porosity of the material may contribute to its strength, flexibility, and elasticity. In some embodiments, the covering may be made of a squishy, moldable, sticky, and/or tacky material to facilitate placement and packing of the covering.

In some embodiments, the covering may be porous to fluid and/or cells, may be biocompatible, and may be resistant to rupture (including should the substance provided therein swell). In some embodiments, the covering with the substance provided therein may be load-bearing. The covering may be resorbable or non-resorbable. The covering may provide increased handling properties, may have irrigation resistance, may have material retention characteristics, and/or may support cellular penetration. Flexibility of the covering may be selected to suit particular applications. In some applications, it may be desirable to have a flexible covering.

If the covering is made from a resorbable material, the covering degrades and disappears after a period of time. The covering thus may be considered a temporary covering. If the covering is not made of a resorbable material, the covering remains in the body. Tissue ingrowth may occur to bind the host tissue to the substance provided within the covering. Tissue ingrowth through and around the covering, between the host tissue and the substance provided within the covering, may be promoted via openings in the covering.

In various embodiments, the covering may comprise a porous material or a mesh material. The size of the pores of the covering may be designed to permit cellular infiltration (approximately several microns to several millimeters), but may also be designed specifically to exclude cells from the inside of the covering (e.g. approximately 0.45 microns) and only allow diffusion of small molecules (proteins and hormones). Thus, the covering may act to control access to the interior of the delivery system by cells. U.S. Patent Application Publication No. 2005/0283255 for Tissue-Derived Mesh for Orthopedic Regeneration describes suitable manners for forming a mesh for use with a covering as provided herein and is herein incorporated by reference in its entirety.

The covering may be formed of a resorbable or nonresorbable, natural or synthetic, biocompatible material. In some embodiments, more than one material may be used, including as multiple layers. For example, in an embodiment comprising two compartments, one or more materials may be used for the first compartment and a different material or materials may be used for the second compartment. For example, one compartment or portions thereof may be made of material or materials that provide a desired property or properties relative to other compartments or portions thereof, such as increased or decreased resorbability or stiffness, or the different compartments or portions thereof may be imparted with different drug delivery properties. Alternatively, all compartments may comprise the same material or mixtures of materials. Where the characteristics of the material are varied between compartments or over the surface of a single compartment, the pores of the first compartment or portion thereof may be larger than the pores of the second compartment.

The covering may comprise any suitable structure for delivering a substance in vivo. Thus, as described, the covering may comprise a mesh. In other embodiments, the covering may comprise a polymeric structure with a chamber provided therein. The chamber may be filled with a substance for delivering in vivo, such as autograft, demineralized bone matrix, or others disclosed herein.

In embodiments comprising more than one compartment, characteristics of the covering material may be varied between compartments. Generally, the porosity, flexibility, strength, or any other characteristic of one compartment may vary from that characteristic of the other compartment. Further, characteristics of the covering may vary at different positions of the covering regardless of compartmental configuration of the covering.

In some embodiments, the covering may expand when placed in the body. Expansion can be provided in at least two ways: the covering may be compressed such that the covering expands when placed in the body or the covering may be made of a material that expands when it comes in contact with water or other bodily fluids, either by way of liquid absorption, or by stretching when the materials inside it absorb liquid and themselves expand. In some embodiments, the covering may comprise a shape memory material such as copper-zinc aluminum-nickel alloy, copper-aluminum-nickel alloy, and nickel-titanium (NiTi) alloy. Reinforcing materials such as cortical bone, calcium phosphates, etc. may be incorporated into the structure of the covering to reinforce it. In other embodiments, the covering may be substantially non-expandable or minimally deformable.

The covering may be configured for specific compressive strength and rigidity by adjusting density and resorption time of the covering. In some embodiments, a coating may be provided over the covering. For example, the coating may be a compound of poly-L-lactide, of polyglycolic acid, or their polymers, or polyhydroxyalkanoates (polyhydroxybutyrates and polyhydroxyvalerates and copolymers). The coating may be selected such that it has a resorption time wherein it is resorbed by the body and the material within the covering is permitted to exit through openings in the covering.

Exemplary Covering Materials

Polymeric material (for example, see U.S. Pat. Nos. 6,696,073, 6,478,825, 6,440,444, and 6,294,187, 7,985,414 and U.S. Patent Publication No. and 2005/0251267, all herein incorporated by reference in their entirety); woven material and braided material (for example, see U.S. Patent Publication No. 2005/0283255, herein incorporated by reference in its entirety); non-woven materials; shape memory material; porous materials; and non-porous materials may be used. In some embodiments, outer particles may be used to contain inner particles; particles may be attached to threads of material, and/or porosity may be added to mesh fibers. In some embodiments, materials may be used for portions of the covering, such as for a compartment of the covering, that are substantially impenetrable.

In some embodiments, the covering may comprise a mesh material. Suitable mesh materials include natural materials, synthetic polymeric resorbable materials, synthetic polymeric non-resorbable materials, and other materials. Natural mesh materials include silk, extracellular matrix (such as DBM, collagen, ligament, tendon tissue, or other), silk-elastin, elastin, collagen, and cellulose. Synthetic polymeric resorbable materials include poly(lactic acid) (PLA), poly(glycolic acid) (PGA), poly(lactic acid-glycolic acid) (PLGA), polydioxanone, PVA, polyurethanes, polycarbonates, polyhydroxyalkanoates (polyhydroxybutyrates and polyhydroxyvalerates and copolymers), polysaccharides, polyhydroxyalkanoates polyglycolide-co-caprolactone, polyethylene oxide, polypropylene oxide, polyglycolide-co-trimethylene carbonate, poly(lactic-co-glycolic acid), and others. See Chen and Wu, "The Application of Tissue Engineering Materials," Biomaterials, 2005, 26(33): p. 6565-78, herein incorporated by reference in its entirety. Other suitable materials include carbon fiber, metal fiber, polyetheretherketones, non-resorbable polyurethanes, polyethers of all types, polyethylene terephthalate, polyethylene, polypropylene, Teflon, and various other meshes. In other embodiments, the covering may comprise non-woven material such as spun cocoon or shape memory materials having a coil shape or shape memory alloys. Alternatively, any of these materials may be used in a non-mesh form.

Generally, the covering may be formed of any natural or synthetic structure (tissue, protein, carbohydrate) that can be used to form a covering configuration. Thus, the covering may be formed of a polymer (such as polyalkylenes, for example, polyethylenes, polypropylenes), polyamides, polyesters, poly(glaxanone), poly(orthoesters), poly(pyrolicacid), poly(phosphazenes), polycarbonate, other bioabsorbable polymer such as Dacron or other known surgical plastics, a natural biologically derived material such as collagen, gelatin, chitosan, alginate, a ceramic (with bone-growth enhancers, hydroxyapatite), PEEK (polyether-etherketone), dessicated biodegradable material, metal, composite materials, a biocompatible textile (for example, cotton, silk, linen), extracellular matrix components, tissues, or composites of synthetic and natural materials, or other. Various collagen materials can be used, alone or in combination with other materials, including collagen sutures and threads. Some examples include polymer or collagen threads woven, or knitted, into a mesh. Other suitable materials include thin polymer sheets molded in the presence of a porogen and having underwent leaching; polymer sheets or naturally derived sheets such as fascia and other collagen materials, small intestinal submucosa, or urinary bladder epithelium, the sheets being punctured to introduce porosity; specific shapes printed using available or future printing technologies; naturally secreted materials such as bacterial cellulose grown within specific molds.

In some embodiments, mesh fibers may be treated to impart porosity to the fibers. This may be done, for example, to PLA, PLGA, PGA, and other fibers. One suitable method for treating the mesh fibers comprises supercritical carbon dioxide treatment to partially solubilize the particles. This treatment may further be carried out for viral inactivation.

Another suitable method for treating the mesh fibers comprises explosive decompression. Explosive decompression generates porosity and leads to controlled permeability. The mesh material further may be loaded with cells, growth factors, or bioactive agents.

In further embodiments, fibers of a mesh material may be treated such as by having particles adhered thereto. The particles may be, for example, bone particles. Thus, in one embodiment, the covering may comprise a plurality of threads formed into a fabric. The threads may have particles adhered thereto. For example, the threads may have particles strung on the thread. In an alternative embodiment, the covering may be formed of a material and the material may be coated with particles.

In yet other embodiments, the covering may comprise a non-porous material, which may be permeable. A non-porous material may be used for later (or delayed) delivery of a substance provided therein. Such substance may comprise, for example, cells, growth factors, or bone morphogenetic proteins. Accordingly, in one embodiment, a delivery system for delayed delivery of cells, growth factors, or bone morphogenetic proteins is provided comprising a non-porous covering.

In particular, in various embodiments, the device may comprise a bioerodible, a bioabsorbable, and/or a biodegradable biopolymer that may provide immediate release, or sustained release of the clonidine. Examples of suitable sustained release biopolymers include but are not limited to poly(alpha-hydroxy acids), poly(lactide-co-glycolide) (PLGA), polylactide (PLA), polyglycolide (PG), polyethylene glycol (PEG) conjugates of poly(alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG and/or PEG may be used as a plasticizer for PLGA, but other polymers/excipients may be used to achieve the same effect. mPEG imparts malleability to the resulting formulations. In some embodiments, these biopolymers may also be coated on the medical device to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the substance from the medical device. In some embodiments, the range of the coating on the medical device ranges from about 5 microns to about 250 microns or 5 microns to about 200 microns to delay release from the medical device.

In various embodiments, the medical device comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

While certain embodiments are described with respect to having mesh characteristics, it is to be appreciated that not all embodiments may have such mesh characteristics. Further, the material used for the covering and its characteristics may be selected for specific applications. For example, in some embodiments, the covering may be formed of a resorbable material, such as formed as a resorbable container or capsule. Such resorbable material may be useful in delivering, for example, antibiotic to a site by an outer resorbable material, and then gradually exposing inner graft material after the infection is cleared. In such embodiments, the delivery system comprises a temporary delivery system.

Functional Material Characteristics

The covering material may have functional characteristics. Alternatively, other materials having functional characteristics may be incorporated into the covering. Functional characteristics may include radiopacity, bacteriocidity, source for released materials, tackiness. Such characteristics may be imparted substantially throughout the covering or at only certain positions or portions of the covering.

Suitable radiopaque materials include, for example, ceramics, mineralized bone, ceramics/calcium phosphates/calcium sulfates, metal particles, fibers, iodinated polymer or mixtures thereof. Other techniques for incorporating a biocompatible metal or metal salt into a polymer to increase radiopacity of the polymer may also be used. Suitable bacteriocidal materials may include, for example, trace metallic elements. In some embodiments, trace metallic elements may also encourage bone growth.

Functional material, such as radiopaque markers, may be provided at one or more locations on the covering or may be provided substantially throughout the covering. Thus, for example, in a tubular covering, a radiopaque marker may be provided at a tip of the tubular covering. Such marker may facilitate placement of the covering. Radiopaque materials may be incorporated into the covering and/or into the substance for delivery by the covering. Further, radiopaque materials may be provided at only some locations on the covering such that visualization of those locations provides indication of the orientation of the covering in vivo.

The covering itself may be designed to release materials during degradation of the covering material. Thus, bone morphogenic proteins (BMPs), growth factors, antibiotics, angiogenesis promoting materials (discussed more fully below), bioactive agents (discussed more fully below), or other actively releasing materials may be incorporated into the covering material such that as the covering material is degraded in the body, the actively releasing material is released. For example, an actively releasing material may be incorporated into a biodegradable polymer covering such as one manufactured of a biodegradable polyester such as poly (lactic acid) (PLA), poly(glycolic acid) (PGA), poly(lactic-co-glycolic acid) (PLGA), or polyhydroxyalkanoates (polyhydroxybutyrates and polyhydroxyvalerates and copolymers). In some embodiments, poly(ethylene glycol) (PEG) may be incorporated into the biodegradable polyester to add hydrophilic and other physico-chemical properties to enhance drug delivery. In some embodiments, composites of allograft bone and biodegradable polymers (for example, PLEXUR™ products available from Osteotech) may be used in the covering.

In some embodiments, the covering may comprise a material that becomes tacky upon wetting. Such material may be, for example, a protein or gelatin based material. Tissue adhesives, including mussel adhesive proteins and cryanocrylates, may be used to impart tackiness to the covering. In further examples, alginate or chitosan material may be used to impart tackiness to the covering. In further embodiments, an adhesive substance or material may be placed on a portion of the covering or in a particular region of the covering to anchor that portion or region of the covering in place at an implant site.

In one embodiment of a covering comprising two compartments, first and second materials may be used for the first and second compartments, respectively. The first material may release or expose a growth factor according to a first rate and the second material may release a growth factor according to a second rate. Further, the growth factors released by the first and second compartments may be the same or may be different. For example, an angiogenic growth factor may be provided with the first compartment and an osteoinductive growth factor may be provided with the second compartment.

Mesh Formulation

Any suitable technique may be used for forming a material for the covering. Generally, the material may be formed as a sheet, as a mesh, or in other configuration. In some embodiments, the material may be a textile type material. Thus, for example, the material may be formed using a textile approach such as be weaving, rug making, knitting. Such formation may be by a mechanical or industrial method. In another embodiment, a substantially solid sheet may be formed and may be treated to assume a configuration penetrable by cells, fluids, and proteins. For example, the sheet may be perforated, may be expanded to create openings, or other. Also, it would be perfectly suitable to take a thin sheet of the covering material, and to perforate it, expand it to create openings, or otherwise make it penetrable by cells, fluids and proteins.

In one embodiment, elongated bone-derived particles or fragments of small intestinal submucosa may be combined longitudinally into three small bundles, each having, for example, from about 1 to about 3 tissue particles. The three bundles may then be braided. Various methods of braiding and types of braids any of which may be useful in producing the material of the invention herein are also useful in the delivery systems of this application. The ends of the braided tissue-derived particles may then be glued together using a fixation agent to prevent their unraveling, or they may be held together with a biocompatible polymer or metal band.

In an alternative embodiment, bone-derived particles are combined with a solvent to form a material. Exemplary solvents include water, lower alkanols, ketones, and ethers and mixtures of any of these or other materials. The material may then be extruded at an appropriate temperature and pressure to create a thread. Threads may also be produced by spinning, drawing, rolling, solvent-extruding, cutting or laser cutting from a sheet or bar stock. The material may alternatively be cast or molded into a solid sheet or bar stock and then cut into thin threads. These may be used immediately or woven into a mesh. Alternatively or in addition, they may be spliced, wrapped, plied, cabled, braided, woven, or some combination of these. The material may be shaped by thermal or chemical bonding, or both. In one embodiment, a portion of the solvent is removed from the material before extrusion.

Alternatively or in addition, the material may be cast as a slurry, extruded, or molded. A variety of materials processing methods will be well known to those skilled in the art. For example, the material may be solvent cast using a press such as a Carver press to spread the material into a film. Solvent evaporation will yield a porous film. Alternatively, the material may be compression molded into a film. The mesh size or porosity of the film will depend on the thickness of the film and the viscosity of the precursor and can be easily manipulated by one skilled in the art. Where elongated particles are used in an extruded aggregate, they will tend to be aligned roughly parallel to one another.

In an alternative embodiment, a thread of a biocompatible natural or synthetic material, for example, polylactide or collagen, may be coated with tissue-derived or other elements, for example, by dubbing. For example, a polymer fiber may be coated with an adhesive, for example, lecithin, and bone particles or other osteoconductive or osteoinductive fibrils allowed to adhere to the thread. The thread may then be twisted on itself or with a second or a plurality of similarly treated threads. Alternatively or in addition, the threads may be braided. The adhesive may be a lipid that is waxy at room temperature, for example, a di- or tri-glyceride that is solid at room temperature. Alternatively or in addition, the adhesive may be a phosphocholine or phosphatidylcholine. In some embodiments, the adhesive is a material that binds both the thread and the material that is used to coat the thread (e.g., bone particles) but that does not degrade either. Non-aqueous adhesives may improve the stability of the final aggregate as compared to aqueous adhesives.

Suitable fibers may be formed utilizing well known techniques, including braiding, plying, knitting, weaving, felting, that are applied to processing natural fibers, for example, cotton, silk, and synthetic fibers made from synthetic bioabsorbable polymers, such as poly(glycolide) and poly(lactic acid), nylon, cellulose acetate. In some embodiments, collagen thread is wound onto cylindrical stainless steel spools. The spools are then mounted onto the braiding carousel, and the collagen thread is then assembled in accordance with the instructions provided with the braiding machine. In one particular run, a braid was prepared of four collagen threads, which consisted of two threads of non-crosslinked collagen and two threads of crosslinked collagen. One skilled in the art will recognize that these techniques may be applied to the other fibrous materials described herein.

Fibers and more evenly dimensioned particles may also be plied into yarns using the same methods and same machinery known to those skilled in the art in plying threads made out of other material, such as cotton, polyester. Four collagen threads were twisted together. Three of the resultant 4-ply strands were then twisted together in the opposite direction, and then 5 of the resultant 12 ply strands were twisted in the opposite direction.

Elongated materials including multistranded materials, for example braids, plied yarns, cables, may be knitted into tubular or flat fabrics by using techniques known to those skilled in the art of producing fabrics manufactured from other types of threads. Various biologically active substances can be incorporated in, or associated with, the braided, knitted, or woven materials. Particles and fibers and materials of these (including multistranded materials) may alternatively or additionally be assembled into a material by non-woven methods such as laying, needle-punching, and hooking (as for a rug). For example, a thread may be attached to another thread or a pressed film.

Regardless of the assembly method, the material shape, mesh size, cable thickness, and other structural characteristics, such as architecture, may be customized for the desired application. For example, where a two dimensional aggregate is used to retain a thixotropic material within a gap, a tight weave is preferred to prevent leakage. To optimize cell or fluid migration through the mesh, the pore size may be optimized for the viscosity and surface tension of the fluid or the size of the cells. For example, pore sizes on the order of approximately 100-200 µm may be used if cells are to migrate through the mesh. Mesh size may be controlled by physically weaving strands of the material by controlling the ratio of solvent to solids in a precursor material.

Cells may be seeded onto the material, or contained within it. In one embodiment, cells may be encapsulated in a matrix such as alginate or collagen gel and the capsules placed on the material. Seeded materials generally do not need to be incubated for long periods of time in solutions that could partially dissolve the binding agent. Instead, the capsules may be placed on the material or covering shortly before implantation. In another embodiment, cells are simply mixed with a gel which is then combined with the material. Alternatively, a material or covering may be cultured with cells before implantation. In one embodiment, thicker materials are used for culturing to increase mechanical integrity during implantation. Any class of cells, including connective tissue cells, organ cells, muscle cells, nerve cells, and stem cells, may be seeded onto the implant. In an exemplary embodiment, connective tissue cells such as osteoblasts, osteoclasts, fibroblasts, tenocytes, chondrocytes, and ligament cells and partially differentiated stem cells such as mesenchymal stem cells and bone marrow stromal cells are employed.

III. Covering Configuration or Form

The shape, configuration, or form of the covering may be selected for particular applications. Such shape and configuration may include, for example, the basic shape of the covering (for example, a cylinder or a bag), whether the covering has a single or a plurality of compartments, and whether the covering includes attachment mechanisms. The covering (or delivery system) may be configured to conform to surrounding bony contours of the space in which it is placed.

Form

In various embodiments, the covering may be formed of as a mesh and may comprise a woven material. The woven material may have varying degrees of permeability. It may be permeable, semi-permeable, or non-permeable. Permeability may be with respect to cells, to liquids, to proteins, to growth factors, to bone morphogenetic proteins, or other. In further embodiments, the material may be braided.

In alternative embodiments, the covering may comprise a substantially solid structure, such as a polymer structure with a chamber, or a spun cocoon.

Shape

The covering may have any suitable configuration. For example, the covering may be formed as a ring, a cylinder, a cage, a rectangular shape, a mesh, a suture-like wrap, a continuous tube, or other configuration. In specific embodiments, the covering may be formed as a thin tube designed to be inserted through catheters or an introducer tube, a rectangular shape designed to fit adjacent to spinal processes for posterolateral spine fusion, a cube like structure designed to fit between vertebral bodies or within cages for interbody spinal fusion, a tube-like shape where the ends are designed to be fitted onto nonunion long bone defects, relatively flat shapes designed to fill cranial or maxillofacial defects, rectangular structures designed for osteochondral defects, structures pre-shaped to fit around various implants (for example, dental, doughnut with hole for dental implants), or relatively elastic ring-like structures that will stretch and then conform to shapes (for example, rubber band fitted around processes). In an embodiment wherein the covering is formed as a cage, the cage may comprise a plurality of crossed filaments which define between them a series of openings for tissue ingrowth. Any of these shapes may be used for a covering comprising a plurality of compartments. For example, in a tubular embodiment, the tube may be formed into a plurality of compartments by tying a cord around the tube at one or more points, or by other suitable mechanism such as crimping, twisting, knotting, stapling, sewing, or other. The configuration of the covering may be determined by the substance to be provided within the covering. For example, if the substance to be contained comprises fibers, the covering may be formed as strings or sutures that are wrapped around the fibers.

Compartments

Single Compartment

Figure 1:
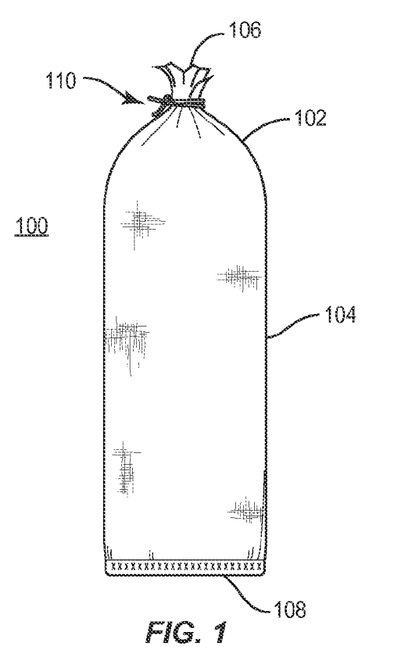
FIG. 1 illustrates a side view of a delivery system comprising a covering having an elongated containment portion, a sealed end, an open end and a closing member in accordance with one embodiment of the present disclosure.

An osteogenic material delivery system 100 in accordance with one embodiment is depicted in FIG. 1. As shown in FIG. 1, delivery system 100 comprises a single compartment covering 102 having an elongated containment 104 for housing a substance for delivery to a surgical site. Elongated containment portion 104 has a first and second end 106, 108. As further illustrated in FIG. 1, first end 106 is open and configured to receive autograft or allograft; second end 108 is sealed and comprises mesh or other sealable material.

Elongated containment portion 104 comprises a length, width and cross section which may vary depending on the application for the covering. The cross section can be tubular or cylindrical and in alternative embodiments, any cross-sectional shape, such as a generally circular, oval, rectangular, generally square, or any other suitable shape may be used.

In other embodiments as shown in FIGS. 1 to 6, coverings 102, 202, 302, 402, 502 and 602 comprise a mesh material and the delivery system can be a mesh bag. Within these coverings or mesh bags, there is provided a particulated substance such as milled bone or DBM particles/fibers, wherein the ratio of DBM fibers to DBM chips is about 30:70.

In various embodiments, the covering may be configured to facilitate placement of graft material in the covering. For example, in the embodiments illustrated in FIGS. 1 to 8, the delivery systems also comprise a closing member, which can be drawing strings, stitches, sutures, heat seals, adhesion, pressure fittings, coil ring, twist tie or combinations thereof. As illustrated in FIG. 1, closing member 110 can be a suture located proximate open end 106 of container 104.

Figure 2:
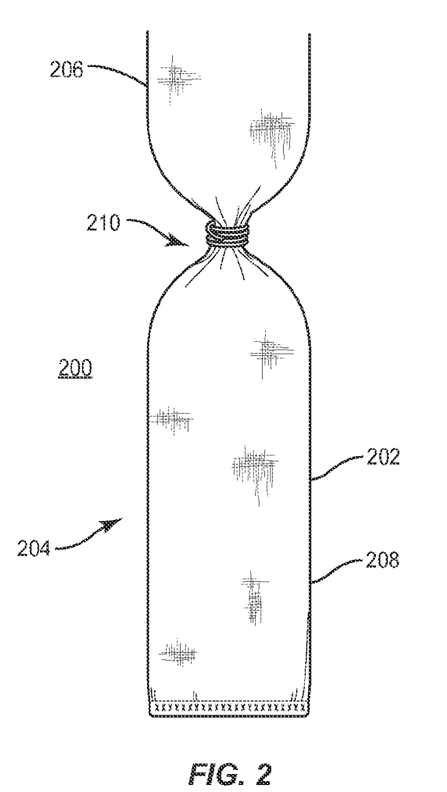
FIG. 2 illustrates a side view of a delivery system comprising a covering such as a porous mesh bag having an elongated containment and a closing member defining an upper portion of the containment and a lower portion of the containment accordance with another embodiment of the present disclosure.

In other embodiments, as illustrated in FIG. 2, closing member 210 can be slidably adjusted over the length of container 204 or can be attached after a portion of container 204 has been filled with bone material either prior to or during a surgical procedure. In FIG. 2, closing member 210 can incorporate a geometric ring providing a stiffening design so that container or pouch 204 can remain in an open position for filling. On filling, the surgeon can twist the upper portion of pouch 204 and fold it over the lower portion, a maneuver facilitated by the closing ring such that the pouch is closed without the need for additional suturing.

Figure 3:
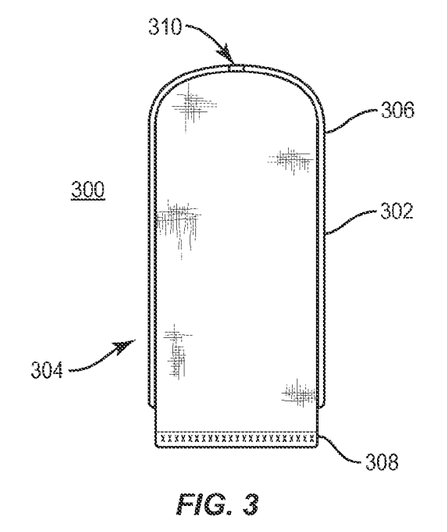
FIG. 3 illustrates a top view of a delivery system comprising a covering having an elongated containment and a closing member, wherein the upper portion of the containment is folded over the lower portion of the containment in accordance with an embodiment of the present disclosure.

As further illustrated in the embodiments of FIGS. 2 and 3, in some embodiments, closing members 210 or 310 define upper portions 206, 306 and lower portions 208, 308 of containers 204 or 304, respectively. Upon closing lower portion 208, 308, with closing members 210, 310, upper portions 206, 306 can be folded over lower portions 208, 308 and, thereafter inserted at a desired surgical site. In other embodiments, the closing member can be omitted and upper portions 206, 306 can be twisted at a selected location and then folded over lower portions 208, 308 of containers 204 or 304, respectively.

Figure 4:
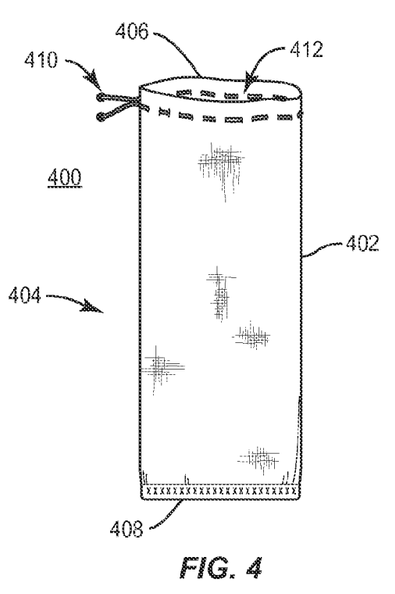
FIG. 4 illustrates a side view of a delivery system comprising a covering such as a mesh bag comprising a closed end and an open end that can be closed by draw strings in accordance with another embodiment of the present disclosure.
Figure 5:
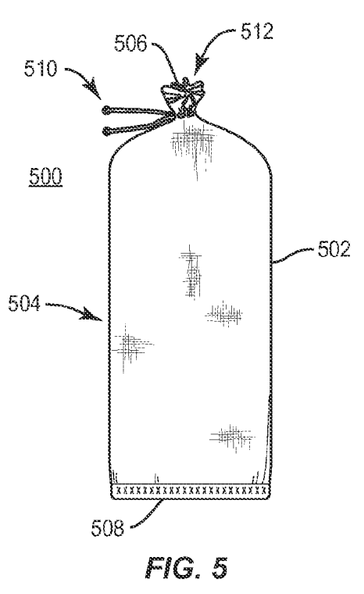
FIG. 5 illustrates a side view of the delivery system comprising a mesh bag having an open end that can be closed by draw strings in accordance with another embodiment of the present disclosure.
Figure 6:
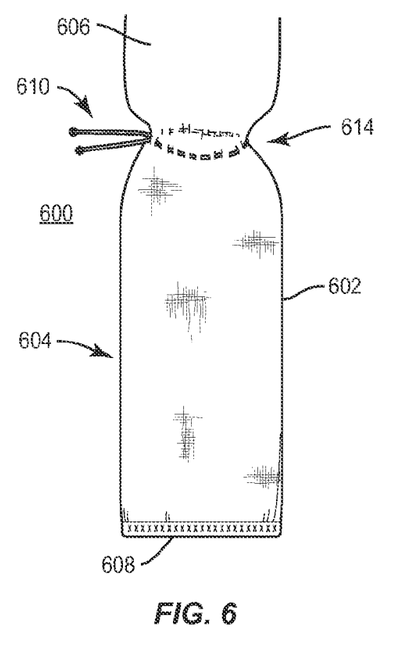
FIG. 6 illustrates side view of the delivery system wherein the draw string is positioned about midway the elongated container in accordance with another embodiment of the present disclosure.

In other embodiments illustrated in FIGS. 4 to 6, coverings 402, 502 and 602 can be closed with closing members comprising drawstrings 410, 510 or 610 located proximate openings 412, 512, about a midway location 614 as illustrated in FIG. 6 or at any desirable location along the elongated containment. In the embodiment illustrated in FIG. 6, upon closing with drawstring 610, upper portion 606 can fold over lower portion 608 of containment 604 as more specifically illustrated in FIG. 3.

Figure 7:
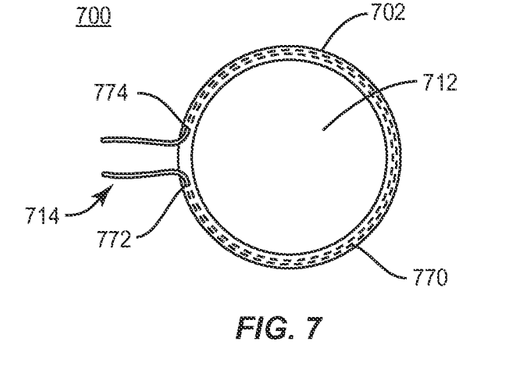
FIG. 7 illustrates a top view of a delivery system according to another aspect of the present application.

In various embodiments, as illustrated in FIG. 7, in an embodiment of this disclosure, drawstrings 714 are positioned around the perimeter of covering 702 proximate opening 712 of covering 702 slidably received in casing or sleeve 770 so that when the end portions of the drawstring 714 are pulled out of the drawstring casing 770 through the two apertures 772, 774, the periphery of covering 702 gathers adjacent the casing to permit the periphery of covering 702 to reduce in size sufficiently to enclose the autograft chips or other graft material therein.

Figure 8:
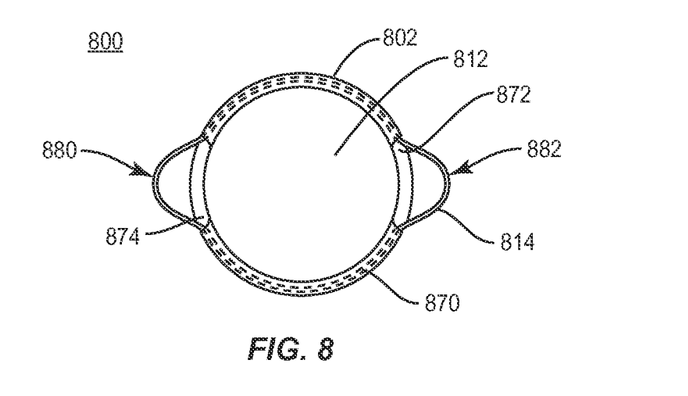
FIG. 8 illustrates a top view of a delivery system according to yet another aspect of the present application.

In another embodiment, as illustrated in FIG. 8, drawstring 814 can be continuous, slidably received in casing 870 and has two loops 880, 882 which extend as oppositely disposed segments around the outside perimeter of the covering 802 at apertures 872, 874 of casing 870. Upon pulling loops 880 and 882, drawstring 814 gathers the periphery of covering 802 adjacent casing 870 to permit the periphery of covering 802 to reduce in size sufficiently to enclose the autograft chips or other graft material therein.

In various other embodiments, the drawstrings used to close the opening of the covering can be wires made of nitinol or any other shape memory alloy. For example, nitinol wires can be slidably received in the casing around the perimeter of the opening of the cover and upon closing the nitinol wires would relapse to a closed position thereby securing the allograft chips or other graft material inside the covering.

With further reference to FIG. 1, one or both ends 106, 108 of elongated containment 104 may contain an attachment or coupling mechanism (not shown) to attach the covering to skeletal or soft tissue proximate to a surgical site. Any suitable attachment mechanism can be used, such as a tab, loop, tack or other structure adapted for attachment at the site. Also, for example, a covering may include a hook-and-eye (Velcro) portion.

In certain other embodiments only one end 108 of the covering or mesh bag 102 is sealed while the other is open to provide easy access for mixing DBM particles/fibers with autologous milled bone or growth factor before or during the surgical procedure. Subsequently, the covering or mesh bag can be closed by various mechanisms including draw strings as shown in FIGS. 4 and 5, sutured or heat seal closed. The draw string can be sequentially or diagonally stitched or in any other pattern configured to close the mesh bag after all the materials were added and prior to placing at a surgical site.

Closing Mechanism

In various embodiments closing mechanisms useful for the delivery systems described herein comprise drawing strings, stitches, sutures, wing sutures, heat seals, adhesion, pressure fittings, coil ring, twist tie or combinations thereof. Closing mechanisms comprise a material selected from bioerodible polymers, bioabsorbable polymers, biodegradable biopolymers, synthetic polymers, copolymers or combinations thereof. In some embodiments, sutures useful as closing member for the delivery system described herein include absorbables and non-adsorbable sutures. Absorbable sutures comprises polyglycolic acid, polylactic acid, and polydioxanone, and caprolactone. Non-absorbables sutures include sutures made of nylon and polypropylene. Coil rings can be made of surgical stainless steel or nitinol material, which upon closing can relapse to a closed position.

Attachment Mechanisms

Generally, any combination of mechanical, physical, chemical, or biological attachment mechanisms may be used. The covering may be configured with structures to permit attachment at the surgical site, such as to skeletal tissue or to soft tissue structures, or for attachment to other coverings, or for attachment to adjacent implantable medical devices or products (such as a rod or screw or cross-brace of a pedicle screw fixation system, a hip prosthesis, a bone plate, and the like). Generally, the attachment mechanism may be used to retain the covering at the surgical site and any mechanisms capable of doing so may be used. The attachment may be to bone or to adjacent tissues such as muscle, tendon, or ligament. Where the covering retains a bone graft substance, the covering may be held in a relatively stable position relative to bone (or relative to the surgical site or surgical defect) to promote bone growth. Accordingly, in some embodiments, the delivery system may be suitable for assisting in attaching tendons, artificial tendons, or ligaments to bone or other structure.

Chemical attachment mechanisms may comprise, for example, a bioadhesive or glue, cement, tape, tissue adhesives, or similar mechanism. Chemical attachment mechanisms may further comprise mechanisms that facilitate crosslinking. In further embodiments, attachment mechanisms such as crimping, welding, soldering, or brazing may be used. Further, attachment may be achieved via friction.

In some embodiments, biological attachment may be via mechanisms that promote tissue ingrowth such as by a porous coating or a hydroxyapatite-tricalcium phosphate (HA/TCP) coating. Generally, hydroxyapatite bonds by biological effects of new tissue formation. Porous ingrowth surfaces, such as titanium alloy materials in a beaded coating or tantalum porous metal or trabecular metal may be used and facilitate attachment at least by encouraging bone to grow through the porous implant surface. These mechanisms may be referred to as biological attachment mechanisms.

Any of the various attachment mechanisms may be provided as part of the covering or may be supplied separately. In various embodiments, the attachment mechanisms may be integral to the covering. Alternatively, the attachment mechanisms may be secured to the covering, for example, by stitching, welding, crimping, or other. The attachment mechanisms may have any suitable geometric configuration and may optionally include apertures for receiving other components for coupling in vivo, such as an aperture for receiving a screw. Thus, for example, an attachment mechanism may be provided configured for receiving an anchor for fixation to bone. Generally, any number of attachment mechanisms may be provided at any suitable location on the covering.

The attachment mechanisms may be manufactured of the same material as the portion of the covering to which it is coupled or may be manufactured of a different material from the portion of the covering to which it is coupled. The attachment mechanism may be resorbable or nonresorbable. The material of the attachment mechanism may be selected to allow anchoring the covering to an adjacent covering having a complementary attachment mechanism or to another structure. In various embodiments, the attachment mechanism may comprise, allograft, synthetic materials, demineralized bone, nondemineralized bone, other material, or combinations of these. The shape and size of the attachment mechanism may be selected based on application.

In some embodiments, the covering may be tubular and have threaded ends such that the ends may be threaded with a reciprocal thread of a further device or implant. For example, the covering may be used with interference screws. In some embodiments, the covering may include extensions or tabs that may be used for wrapping around or suturing to the surgical site. Alternatively, the covering may be sutured directly to the surgical site. The ends of the covering may be presealed or may be sealed after introduction of contents. Sealing may be done by using adhesives, heating, solvent treatment, suturing, knotting, or any other means.

Packing

The substance may be packed in the covering at any suitable density. For some applications, the substance may be loosely packed in the covering to enhance manipulability. In some embodiments, the material may be packed in the covering such that the covering retains flexibility and may be folded over itself. In other applications, the substance may be tightly packed in the covering to provide a relatively stiff delivery system, and it may be weight bearing. In some embodiments, the covering may be configured to facilitate placement of graft material in the covering as was illustrated in FIGS. 1-8 described herein.

IV. Substance for Delivery by Covering

A substance is provided in the covering, before or during surgery (as described below), for delivery in vivo. Generally, the substance or material may be homogenous or heterogeneous. The substance or material may be selected to exhibit certain gradients. For example, the substance or material may be selected to exhibit a gradient to guide, lure, or attract cells along a pathway. Such gradient may comprise a cell gradient, a cell type gradient (for example transitioning from bone cells to cartilage cells or transitioning from bone cells to tendon cells), a gradient of conductivity, or a gradient of density/porosity. In some embodiments, the substance or material may comprise a sequence of ingredients.

The covering may be used to deliver a substance comprising any suitable biocompatible material. In specific embodiments, the covering may be used to deliver surface demineralized bone chips (cortical or cancellous), optionally of a predetermined particle size, demineralized bone fibers, optionally pressed, and/or allograft. For example, in certain embodiments, the ratio of DBM fibers to DBM chips is about 30:70. In various embodiments, the ratio of fibers to chips, particles or powders can be from about 5, 10, 15, 20, 25, 30, 35, 40, or 45 fibers to about 30, 35, 40, 45, 50, 55, 60, 65, or 70 chips.

In some embodiments, the demineralized bone material in the covering comprises from about 1 to about 70 micrometers particle size range or from about 125 to about 250 micrometer particle size range.

In some embodiments, the covering may have a modulus of elasticity in the range of about $1\times10^2$ to about $6\times10^5$ dynes/$cm^2$, or $2\times10^4$ to about $5\times10^5$ dynes/$cm^2$, or $5\times10^4$ to about $5\times10^5$ dynes/$cm^2$. After the cover is administered to the target site, the covering may have a modulus of elasticity in the range of about $1\times-10^2$ to about $6\times10^5$ dynes/$cm^2$, or $2\times10^4$ to about $5\times10^5$ dynes/$cm^2$, or $5\times10^4$ to about $5\times10^5$ dynes/$cm^2$.

For embodiments wherein the substance is biologic, the substance may be autogenic, allogenic, xenogenic, transgenic, or combinations of these. Each of these tissue types includes any tissue of bone origin, connective tissue origin, or any collagen containing material including organ tissues. Other suitable materials that may be positioned in the covering include, for example, protein, hormones, nucleic acid, carbohydrate, lipids, collagen (autograft, allograft, or xenograft from musculoskeletal or organ systems), allograft bone, autograft bone, cartilage stimulating substances, allograft cartilage, TCP, TCP/calcium sulfate, calcium carbonate, calcium phosphates, bioactive glasses, glass ceramics, magnesium phosphates, phosphates containing any biocompatible metal ion, porous implants of all types including trabecular metal, biocompatible metals including stainless steel, cobalt-chrome, titanium, titanium alloys, polymers such as polylactic acid, polyglycolic acid, polycaprolactone, polyglycolide-co-caprolactone, polyethylene oxide, polypropylene oxide, polyglycolide-co-trimethylene carbonate, poly (lactic-co-glycolic acid), poly-L-lactide, polyethylene glycol, polyetheretherketones, polyurethanes, polyethers of all types, poly ethylene terephthalte, polyethylene, polypropylene, Teflon, chondroitin sulfate, hyaluronic acid and its salts, chitosan and derivatives, natural polymers such as silk, collagen, polysaccharides, polyhydroxyalkanoates, polymers combined with bone or collagen or both from any source (allograft, xenograft, transgenic, autograft), hydroxyapatite, calcium sulfate, polymer, nanofibrous polymers, growth factors, carriers for growth factors, growth factor extracts of tissues, demineralized bone matrix, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, platelets, activated platelets, antibiotics, substances with antimicrobial properties, or combinations of any of the above. In accordance with one embodiment, the substance is a bone matrix composition such as described in U.S. patent application Ser. No. 12/140,044 and U.S. Patent Publications Nos. 2007/0098756 and 2007/0110820 all for Bone Matrix Compositions and Methods, herein incorporated by reference in their entireties. Suitable materials for preparing biocomposites for placement in the covering are disclosed in U.S. Patent Publication Nos. 2007/0191963, 2006/0216323, and 2005/0251267, U.S. Pat. Nos. 6,696,073, 6,478,825, 6,440,444, and 6,294,187, all herein incorporated by reference in their entireties for all purposes.

In some embodiments, the substance or material for delivery may comprise a biodegradable polyester such as poly (lactic acid) (PLA), poly(glycolic acid) (PGA), poly(lactic-co-glycolic acid) (PLGA), or polyhydroxyalkanoates (polyhydroxybutyrates and polyhydroxyvalerates and copolymers), polysaccharides, polyhydroxyalkanoates, polyglycolide-co-caprolactone, polyethylene oxide, polypropylene oxide, and polyglycolide-co-trimethylene carbonate. In some embodiments, poly(ethylene glycol) (PEG) may be incorporated into the biodegradable polyester to add hydrophilic and other physico-chemical properties to enhance drug delivery. In some embodiments, composites of allograft bone and biodegradable polymers (for example, PLEXUR® products available from Osteotech) may be delivered by the covering.

In some embodiments, the substance may be pressed before placement in the covering. A substance provided within the covering may be homogenous, or generally a single substance, or may be heterogeneous, or a mixture of substances. In some embodiments, the substance may be designed to expand in vivo. U.S. Patent Publications No. 2008/0091270 describes an osteoimplant that expands in vivo and is herein incorporated by reference in its entirety. Such an embodiment may be used to fill a space and create contact with congruent surfaces as it expands in vivo, for example for interbody fusion. Thus, in some embodiments, the delivery system may be used in the disc space, between implants, or inside a cage. In some embodiments, the substance may include a natural and/or synthetic expandable material. The expandable material may comprise bone particles, a polymer, a hydrogel, a sponge, collagen, or other material. In various embodiments, the expandable material comprises bone allograft comprising demineralized bone particles, and the demineralized bone particles may be a blend of cortical and cancellous bone. For example, the expandable material may comprise demineralized cortical fibers and demineralized cancellous chips, wherein the demineralized cancellous chips may create a healthy matrix for the incorporation of new bone and add advanced expansion characteristics.

In addition to bone particles, an expandable polymer, a collagen sponge, compressed and/or dried hydrogels, or other materials may be used. In addition to expansion properties, the material may exhibit osteoinductive and/or osteoconductive properties. For example, cancellous bone particles may exhibit osteoconductive properties while demineralized cortical bone particles may exhibit osteoinductive properties.

The expandable material may be compressed during formation to aid in subsequent expansion. Generally, increased compression leads to increased expansion characteristics in the osteoimplant. Compressed materials and certain non-compressed materials may be constrained such that, absent the constraint, the material is free to expand. A constrained material is one that embodies energy, such as a bent, spring-loaded, or coiled material, or any other material that is artificially prevented from expanding or conforming to its natural configuration. The expandable material may include a covering material that partially or wholly surrounds the material. The covering material may be provided also expand as the expandable material expands.

Expansion may be activated in any suitable manner. For example, expansion may be activated by exposure to air, water, blood, heat, removal of a constraint, or otherwise. In one embodiment, the expandable material may be provided compressed and dried. Upon exposure to liquid in vivo, the expandable material may expand. In another embodiment, the expandable may be compressed and at least partially constrained by a covering material. Upon exposure to liquid in vivo, the covering material may expand or disintegrate, as the expandable material expands. The expandable material may expand as a function of time. In yet another embodiment, the expandable material may have a first state at approximately 60° F. and an expanded state at approximately 98° F. such that, upon implantation in vivo and exposure to body heat, the expandable material may expand. In a further embodiment, the expandable material may be vacuum-sealed during manufacture and, when unsealed and exposed to air, the expandable material may expand.

The covering retains the substance in place by pressure against the covering. The covering thus may, in some embodiments, maintain particles of substance in close proximity (for example, where the covering retains a substance comprising bone particles). Generally, the ratio of covering material to substance for placement within the covering may be low. For example, in some embodiments, the ratio of covering material to substance, by weight, may be approximately 1:1,000, 1:100, 1:50, 1:25, 1:1, or any suitable ratio that may be higher or lower than these.

In some embodiments the substance delivered by the covering may include or comprise an additive such as an angiogenesis promoting material or a bioactive agent. It will be appreciated that the amount of additive used may vary depending upon the type of additive, the specific activity of the particular additive preparation employed, and the intended use of the composition. The desired amount is readily determinable by one skilled in the art. Angiogenesis may be an important contributing factor for the replacement of new bone and cartilage tissues. In certain embodiments, angiogenesis is promoted so that blood vessels are formed at an implant site to allow efficient transport of oxygen and other nutrients and growth factors to the developing bone or cartilage tissue. Thus, angiogenesis promoting factors may be added to the substance to increase angiogenesis. For example, class 3 semaphorins, e.g., SEMA3, controls vascular morphogenesis by inhibiting integrin function in the vascular system, Serini et al., Nature, (July 2003) 424:391-397, incorporated by reference herein, and may be included in the recovered hydroxyapatite.

In accordance with some embodiments, the substance may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; demineralized bone powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin; bacteriaphages; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and anti-adhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other means; tissue transplants; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD. A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996; and the United States Pharmacopeia-25/National Formulary-20, published by the United States Pharmacopeia Convention, Inc., Rockville Md., 2001.

In some embodiments the drug can be a statin. Examples of a useful statin for treatment of pain and/or inflammation include, but is not limited to, atorvastatin, simvastatin, pravastatin, cerivastatin, mevastatin, velostatin, fluvastatin, lovastatin, rosuvastatin and fluindostatin (Sandoz XU-62-320), dalvastain, eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin. Anti-inflammatory agents also include those with anti-inflammatory properties, such as, for example, amitriptyline, carbamazepine, gabapentin, pregabalin, clonidine, or a combination thereof.

Unless otherwise specified or apparent from context, where this specification and the set of claims that follows refer to a drug (e.g., an anti-inflammatory agent, analgesic, or the like) this disclosure is also referring to a pharmaceutically acceptable salt of the drug including stereoisomers. Pharmaceutically acceptable salts include those salt-forming acids and bases that do not substantially increase the toxicity of the compound. Some examples of potentially suitable salts include salts of alkali metals such as magnesium, calcium, sodium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

Generally, any suitable substance or material may be delivered using coverings as provided herein. Such substances may include bone, cartilage, tendon, ligament, muscle, skin, nerve, collagen, calcium sulfate ($CaSO_4$), calcium phosphate ($CaPO_4$), βTCP, hydroxyapatite, bioglass, silicon-containing calcium phosphates, cells, autograft, or other.

Particulate Substance

In some embodiments, a particulate substance may be delivered by the covering. For example, the covering may be used to deliver a particulate bone graft.

Growth Factors or Other Active Substances

Growth factors or other active substances may be delivered by the covering. Active substances may include, for example, growth factors such as BMP-2 (Infuse) and/or other growth proteins, as well as drugs, for example, antibiotics. In some embodiments, a carrier for the growth factors or other active substances may be incorporated into the delivery system.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

Sterilization.

The medical device and/or covering may be sterilizable. In various embodiments, one or more components of the medical device and/or covering are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply in the device and/or covering. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device and/or covering. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the medical device and/or covering is included in a gel.

Other methods may also be used to sterilize the device and/or covering and/or one or more components of the device and/or covering, including, but not limited to, gas sterilization, such as, for example, with ethylene oxide or steam sterilization.

Methods of Use.

The covering delivers the substance or substances in vivo. Such delivery may be active, passive, by diffusion, or other. Active delivery may include the degradation or decomposition of the covering with the interaction of body fluids, extracellular matrix molecules, enzymes or cells. It may also include the cleavage of physical and/or chemical interactions of substance from covering with the presence of body fluids, extracellular matrix molecules, enzymes or cells. Further, it may comprise formation change of substances (growth factors, proteins, polypeptides) by body fluids, extracellular matrix molecules, enzymes or cells.

The covering is loaded with the substance for placement in vivo. The covering may be pre-loaded, thus loaded at manufacture, or may be loaded in the operating room or at the surgical site. Preloading may be done with any of the substances previously discussed including, for example, DBM, synthetic calcium phosphates, synthetic calcium sulfates, enhanced DBM, collagen, carrier for stem cells, and expanded cells (stem cells or transgenic cells). Any other suitable method may be used for loading a substance in the covering in the operating room or at the surgical site. For example, the substance may be spooned into the covering, the substance may be placed in the covering using forceps, the substance may be loaded into the covering using a syringe (with or without a needle), or the substance may be inserted into the covering in any other suitable manner. Specific embodiments for loading at the surgical site include for vertebroplasty or for interbody space filler.

In various embodiments, loading in the operating room or at the surgical site can be done with any of these materials and further with autograft and/or bone marrow aspirate by adding the desired material through the filling means or funnel, by gravity using a spoon and/or a plunger to push the material through. In some embodiments, the closing member useful for delivery systems described herein can incorporate a geometric ring which provides a stiffening design so that container or pouch can remain in an open position for filling and the surgeon no longer requires the use of other filling means, such as for example a funnel. (please verify)

For placement, the substance or substances may be provided in the covering and the covering placed in vivo. In one embodiment, the covering is placed in vivo by placing the covering in a catheter or tubular inserter and delivering the covering with the catheter or tubular inserter. The covering, with a substance provided therein, may be steerable such that it can be used with flexible introducer instruments for, for example, minimally invasive spinal procedures. For example, the osteoimplant may be introduced down a tubular retractor or scope, during XLIF, TLIF, or other procedures. In other embodiments, the covering (with or without substance loaded) may be placed in a cage, for example for interbody fusion.

In continuous tube embodiments, the surgeon may divide the tube into the desired number of compartments, using a crimper, heat tool or other. Alternatively, in an embodiment wherein the tube is perforated into a plurality of compartments, the surgeon may select the number of compartments desired and cut along the applicable perforation. In some embodiments, some of the compartments may be prefilled with a substance for delivery and other compartments may be empty for filling by the surgeon. For example, ever other compartment between perforations may be preloaded or filled. The osteoimplant thus may be customized by filling the empty compartments with a desired substance.

The covering may be used in any suitable application. In some embodiments, the covering may be used in healing vertebral compression fractures, interbody fusion, minimally invasive procedures, posterolateral fusion, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others. The delivery system may be used in a minimally invasive procedure via placement through a small incision, via delivery through a tube, or other. The size and shape may be designed with restrictions on delivery conditions. In some embodiments, pieces of the covering can be separated by pulling or tearing force applied along separation assists if present in a multi compartment configuration and the pieces of the covering can be used to surround the bone defect. For examples, 3 pieces of the torn covering can be placed around the bone defect to triangulate bone growth by the influx of cells, in, at or near the bone defect.

In some embodiments, the covering is flexible enough so that the covering can be folded upon itself before it is implanted at, near or in the bone defect.

An exemplary application for using a delivery system as disclosed is fusion of the spine. In clinical use, the covering and delivered substance may be used to bridge the gap between the transverse processes of adjacent or sequential vertebral bodies. The delivery system may be used to bridge two or more spinal motion segments. The covering surrounds the substance to be implanted, and contains the substance to provide a focus for healing activity in the body.

In other applications, the delivery system may be applied to transverse processes or spinous processes of vertebrae.

Generally, the delivery system may be applied to a pre-existing defect, to a created channel, or to a modified defect. Thus, for example, a channel may be formed in a bone, or a pre-existing defect may be cut to form a channel, for receipt of the delivery system. The covering may be configured to match the channel or defect. In some embodiments, the configuration of the covering may be chosen to match the channel. In other embodiments, the channel may be created, or the defect expanded or altered, to reflect a configuration of the covering. The covering may be placed in the defect or channel and, optionally, coupled using attachment mechanisms.

At the time just prior to when the delivery system is to be placed in a defect site, optional materials, e.g., autograft bone marrow aspirate, autograft bone, preparations of selected autograft cells, autograft cells containing genes encoding bone promoting action, can be combined with the covering and/or with a substance provided within the covering prior to or during the surgical procedure. The osteoimplant can be implanted at the bone repair site, if desired, using any suitable affixation means, for example, sutures, staples, bioadhesives, screws, pins, rivets, other fasteners and the like or it may be retained in place by the closing of the soft tissues around it.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An osteogenic material delivery system comprising:
   a covering configured for implantation into a bone defect site, the covering having at least one compartment, the at least one compartment comprising an elongated containment having a first open end and second sealed end opposite each other, the elongated containment defining an opening;
   at least one bone graft substance disposed within the elongated containment, the at least one substance comprising fully demineralized bone matrix fibers and surface demineralized bone chips in a ratio of about 30:70 of fibers to chips, and the size of the fully demineralized bone matrix fibers and surface demineralized bone chips are from about 125 to 250 micrometers;
   a closing member positioned at a location along the elongated containment and adapted to close the elongated containment with the at least one bone graft substance disposed therewithin; and
   an attachment mechanism for retaining the covering at the bone defect site,
   wherein the covering comprises a porous mesh bag, said porous mesh bag retaining the at least one bone graft substance for placement at the bone defect site and for facilitating transfer of cells into and out of the porous mesh bag,
   wherein the closing member comprises drawing strings, stitches, sutures, wing sutures, heat seals, adhesion, pressure fittings, coil ring, twist ties or combinations thereof.

2. A delivery system according to claim 1, wherein the closing member is positioned proximate the opening of the elongated containment.

3. A delivery system according to claim 1, wherein the closing member is positioned at a location effective to define an upper portion of the elongated containment and a lower portion of the elongated containment.

4. A delivery system according to claim 3, wherein upon closing of the closing member, the upper portion is configured to fold over the lower portion of the containment.

5. A delivery system according to claim 1, wherein the elongated containment has a cross sectional shape selected from generally circular or generally oval.

6. A delivery system according to claim 1, wherein the elongated containment has a shape selected from tubular, rectangular, cube or mesh bag.

7. A delivery system according to claim 1, wherein the at least one compartment is unfilled at manufacture and configured to be filled prior to or during the surgical procedure.

8. A delivery system according to claim 1, wherein the at least one substance comprises autograft or allograft.

9. A delivery system according to claim 8, further comprising a second substance, the second substance comprising protein, bone morphogenetic proteins, carbohydrate, lipids, collagen, allograft bone, autograft bone, tricalcium phosphate, hydroxyapatite, growth and differentiation factors, carriers for growth factors, growth factors extracts of tissue, bone marrow aspirate, concentrates of lipid derived or marrow derived adult stem cells, umbilical cord derived stem cells, committed or partially committed cells from osteogenic or chondrogenic lineage, antimicrobials, antibiotics, statins, or combinations thereof.

10. A delivery system according to claim 1, wherein the covering or the closing member or both comprise a material selected from bioerodible polymers, bioabsorbable polymers, biodegradable biopolymers, synthetic polymers, copolymers or combinations thereof.

* * * * *